US008241868B2

(12) United States Patent
Higashiyama et al.

(10) Patent No.: US 8,241,868 B2
(45) Date of Patent: Aug. 14, 2012

(54) PRODUCTION OF POLYUNSATURATED FATTY ACIDS USING CELL TREATMENT METHOD

(75) Inventors: Kenichi Higashiyama, Kobe (JP); Toshiharu Nakajima, Ibaraki (JP)

(73) Assignee: Nippon Suisan Kaisha, Ltd., Chiyoda-ku, Tokyo (JP)

( * ) Notice: Subject to any disclaimer, the term of this patent is extended or adjusted under 35 U.S.C. 154(b) by 1050 days.

(21) Appl. No.: 11/883,517

(22) PCT Filed: Feb. 8, 2006

(86) PCT No.: PCT/JP2006/002589
§ 371 (c)(1),
(2), (4) Date: Aug. 1, 2007

(87) PCT Pub. No.: WO2006/085672
PCT Pub. Date: Aug. 17, 2006

(65) Prior Publication Data
US 2008/0166781 A1 Jul. 10, 2008

(30) Foreign Application Priority Data
Feb. 8, 2005 (JP) .................................. 2005-031918

(51) Int. Cl.
C12N 1/12 (2006.01)
C12P 1/00 (2006.01)
C12P 1/02 (2006.01)
C12P 7/00 (2006.01)
C12P 7/64 (2006.01)

(52) U.S. Cl. .......... 435/41; 435/132; 435/134; 435/171; 435/257.1; 435/946

(58) Field of Classification Search .................. None
See application file for complete search history.

(56) References Cited

U.S. PATENT DOCUMENTS

| 6,238,714 B1 | 5/2001 | Binder et al. |
| 2001/0016342 A1 | 8/2001 | Higashiyama et al. |
| 2003/0143659 A1* | 7/2003 | Bijl et al. ................. 435/67 |

FOREIGN PATENT DOCUMENTS

| CN | 1323904 | 11/2001 |
| EP | 0 522 470 A1 | 7/1992 |
| EP | 0 960 943 | 12/1999 |
| EP | 0 990 694 A1 | 4/2000 |
| EP | 1 050 219 A1 | 11/2000 |
| JP | 63-012290 | 1/1988 |
| JP | 63-044891 | 2/1988 |
| JP | 5-017796 A | 1/1993 |
| JP | 06-153970 | 6/1994 |
| JP | 2000-325024 | 11/2000 |
| JP | 2002-502233 | 1/2002 |
| JP | 2003-048831 | 2/2003 |
| WO | 97/36996 | 10/1997 |
| WO | WO 97/36996 | 10/1997 |
| WO | WO 97/37032 | 10/1997 |
| WO | WO 98/29558 | 7/1998 |
| WO | WO 2000-508888 | 7/2000 |
| WO | WO 01/54510 A1 | 8/2001 |

OTHER PUBLICATIONS

Information Disclosure submission to Japanese Patent Office in Japanese application No. 2005-031918 (Japanese language).
Hideaki Yamada et al., "*Production of Dihomo-γ-linolenic Acid, Arachidonic Acid and Eicosapentaenoic Acid by Filamentous Fungi*," in Industrial Applications of Single Cell Oils 118-138 (David J. Kyle and Colin Ratledge editors, American Oil Chemists' Society, Champaign, Illinois, 1992).
Koza, Shokuhin Kogaku Kiso, (6) "Concentration and Drying", R. Matsuno et al., Korin Press (1988), Chap. 5 (w/ partial translation).
Martin E. de Swaaf et al., "Analysis of Docosahexaenoic Acid Biosynthesis in *Crypthecodinium cohnii* by $^{13}$C labelling and Desaturase Inhibitor Experiments", Journal of Biotechnology, 2003, pp. 21-29, vol. 103.
A. Giménez Gimenez et al., "Downstream Processing and Purification of Eicosapentaenoic (20: 5n-3) and Arachidonic Acids (20:4n-6) from the microalga *Porphyridium cruentum*", Bioseparation, 1998, pp. 89-99, vol. 7, Kluwer Academic Publishers, The Netherlands.
Kenichi Higashiyama et al., "Production of Arachidonic Acid by *Mortierella* Fungi", Biotechnol. Bioprocess. Eng., 2002, pp. 252-262, vol. 7.
International Search Report dated Jan. 26, 2007 in International PCT Application No. PCT/JP2006/302589.
European Search Report dated May 13, 2011, issued in European Application No. EP 10 01 0293.8-1212.
Japanese Office Action mailed Jun. 14, 2011, in Japanese Patent Application No. 2005-031918.

\* cited by examiner

*Primary Examiner* — Debbie K Ware
(74) *Attorney, Agent, or Firm* — Drinker Biddle & Reath LLP

(57) ABSTRACT

A method for isolating one compound or more than one compound from a biomass which contains microorganisms that have produced the compound or compounds, the method comprising the following steps: (a) preparing or obtaining wet cells having an average moisture content of between 30% and 80%; (b) subjecting the wet cells to primary drying to obtain primary dried cells having an average moisture content of between 5% and 50%; (c) subjecting the primary dried cells obtained in (b) to secondary drying to obtain secondary dried cells having an average moisture content of no greater than 10%; and (d) extracting or isolating, purifying and/or refining the compound or each of the compounds from the secondary dried cells obtained in (c).

17 Claims, No Drawings

PRODUCTION OF POLYUNSATURATED FATTY ACIDS USING CELL TREATMENT METHOD

CROSS REFERENCE TO RELATED APPLICATIONS:

This application is the National Stage of International Application No. PCT/JP2006/302589, filed Feb. 8, 2006, and claims benefit of Japanese Application No. 2005-031918, filed Feb. 8, 2005, both of which are herein incorporated by reference in their entirety.

TECHNICAL FIELD OF THE INVENTION

The present invention relates to a microbial biomass which contains microorganisms that produce a compound comprising a polyunsaturated fatty acid as a constituent fatty acid, a crude oil and/or crude phospholipid obtained by extraction from the biomass, and a method for production of a refined oil and/or refined phospholipid obtained by purification of a crude oil and/or crude phospholipid, as well as to foods and beverages, therapeutic nutritional supplements, feeds and pharmaceuticals which incorporate the biomass, fats or oils (crude oils and/or refined oils) and/or phospholipids (crude phospholipids and/or refined phospholipids).

BACKGROUND ART

Biosynthesis of human polyunsaturated fatty acids (hereinafter, "PUFA") occurs for two representative series, the ω3 and ω6 series (where ω represents the number of the carbon atom having the first double bond, counting from the methyl group end of the fatty acid), and in the case of ω6 fatty acids, for example, linoleic acid (18:2 ω6) is converted to γ-linolenic acid (18:3 ω6), dihomo-γ-linolenic acid (20:3 ω6), arachidonic acid (20:4 ω6) and 4,7,10,13,16-docosapentaenoic acid (22:5 ω6), by repeated desaturation and carbon chain elongation.

Similarly, in the case of ω3 fatty acids, α-linolenic acid (18:3 ω3) is converted to eicosapentaenoic acid (20:5 ω3), 7,10,13,16,19-docosapentaenoic acid (22:5 ω3) (docosapentaenoic acid) and 4,7,10,13,16,19-docosahexaenoic acid (22:6 ω3) (docosahexaenoic acid), by repeated desaturation and carbon chain elongation. The ω3 PUFAs eicosapentaenoic acid (hereinafter, "EPA") and docosahexaenoic acid (hereinafter, "DHA") in particular are known to have numerous physiological functions including prophylactic effects against adult diseases such as atherosclerosis and thrombosis or anticancer effects, as well as learning reinforcement effects, and various attempts have been made to utilize them in pharmaceuticals and food for specified health uses. However, PUFAs other than ω3 types (such as ω6 and ω9) have recently also been the subject of attention.

Arachidonic acid constitutes approximately 10% of the fatty acids composing vital organs such as the blood and liver (for example, the fatty acid compositional ratio of the phospholipids in human blood is 11% arachidonic acid, 1% eicosapentaenoic acid, 3% docosahexaenoic acid), and as a major structural component of cell membranes, it contributes to modulating membrane fluidity and performs various metabolic functions, while also playing an important role as a direct precursor of prostaglandins. Recently the roles of arachidonic acid as a nursing infant nutrient and as a constituent fatty acid of endogenous cannabinoids which exhibit neuroactivating effects (2-arachidonoyl monoglycerol, anandamide) have been noted. Normally, ingestion of linoleic acid-rich foods leads to their conversion to arachidonic acid, but since the functions of the enzymes involved in its biosynthesis are reduced in life-style related disease patients and preliminary conditions as well as in infants and the elderly, such individuals tend to be deficient in arachidonic acid; it has therefore been desirable to provide means for its direct ingestion in the form of a constituent fatty acid of fats or oils (triglycerides).

Although fish oils are abundant sources of ω3 PUFAs such as EPA and DHA, ω6 PUFAs such as γ-linolenic acid, dihomo-γ-linolenic acid, arachidonic acid and 4,7,10,13,16-docosapentaenoic acid (22:5 ω6) are virtually unobtainable from traditional fat or oil sources, and therefore fats and/or oils comprising PUFAs as constituent fatty acids (hereinafter referred to as "PUFA-containing fats and/or oils") obtained by fermentation of microorganisms are most commonly used at the current time. For example, methods have been proposed for obtaining fats and/or oils comprising arachidonic acid as a constituent fatty acid (hereinafter referred to as "arachidonic acid-containing fats and/or oils") by culturing of various microorganisms capable of producing arachidonic acid-containing fats and/or oils.

It is known that fats and oils having a high proportion of arachidonic acid constituting the fatty acid portion (hereinafter referred to as "arachidonic acid-rich fats and/or oils") can be obtained by using microorganisms belonging to the genus *Mortierella* (Japanese Unexamined Patent Publication SHO No. 63-44891, Japanese Unexamined Patent Publication SHO No. 63-12290). In recent years, one of the essential uses of arachidonic acid is in the field of nursing infant nutrition, for example, and specifically involves the use of arachidonic acid-containing fats and/or oils obtained by fermentation in infant formula. New effects of arachidonic acid-containing fats and/or oils have also been demonstrated (Japanese Unexamined Patent Publication No. 2003-48831: Composition with prophylactic or ameliorative effect on symptoms and conditions associated with brain function impairment), and these are expected to be in high demand in the future.

Fats and/or oils obtained by culturing of *Mortierella* microorganisms consist largely of triglycerides (approximately 70% or greater) and phospholipids. The edible fats and/or oils are in the form of triglycerides, and for the purpose of the use described above, the original fats and/or oils produced by the cells (fats and oils obtained by extraction from cells, known as "crude oils") are extracted from the cell biomass resulting from culturing of the microorganisms, and then the crude oils are subjected to edible fat/oil refining steps (degumming, deoxidation, deodorization and decolorizing) to obtain refined fats and/or oils without the phospholipids.

Since PUFA- containing fats and/or oils obtained by culturing of *Mortierella* microorganisms accumulate in mycelia, culturing must be carried out to a higher concentration to increase the yield of the PUFA-containing fats and/or oils per culture, for higher economical optimization of the fat/oil production. The PUFA-containing fat and/or oil yield per culture is the product of the cell or mycelial concentration and the PUFA-containing fat/oil content per mycelia, and it is therefore necessary to increase both the cell concentration and the PUFA-containing fat/oil content per culture. The cell concentration can be increased by raising the concentration of the nitrogen source in the culture medium which is normally converted to cell components. The PUFA-containing fat/oil content per mycelia can only be increased by satisfactorily controlling the cellular form and by carrying out the fermentation in the presence of adequate oxygen. Methods reported for controlling the cellular form include optimization of the medium salt composition (Japanese Domestic Re-publication No. 98/029558), while methods of supplying oxygen include pressurized culturing methods and oxygen enriched aerobic culturing methods (Japanese Unexamined Patent Publication HEI No. 06-153970).

Attempts to improve not only the culturing procedure but also the post-culturing cell recovery procedure have been reported as well. For example, one reported method involves acquiring a microbial biomass (20-75% moisture content) and granulating it into granular particles while maintaining the moisture content, and then drying it to a moisture content of below 20%, whereby the granulation facilitates not only drying but also extraction of the target compound (WO97/36996). This publication teaches that an extrusion method is preferred for molding into granular particles, but ordinary extrusion methods do not alter the moisture content in general.

The granular particles are dried by, for example, spray drying, fluidized bed drying, lyophilization drying, belt drying or vacuum drying. Another known method is one in which a culture solution of a *Mortierella* filamentous fungus is filtered to collect the cells, which are then dried and disrupted, and the fats and/or oils are extracted using an organic solvent (CN1323904A), while Yamada et al. have reported a disruption method using a ball mill ("Industrial applications of single cell oils", edited by D. J. Kyle and C. Ratledge, AOCS press (1992) p. 118-138). Thus, although various different cell recovery methods have been published, the drying is invariably accomplished by a single step of conventional drying, whereas no development of using novel driers or using multiple conventional driers has been disclosed. Moreover, no dried microbial biomass processing method has been described.

Despite the fact that the cell recovery procedure is extremely important from the standpoint of loss or reduction of the microbial fats and/or oils and of microbial fat/oil quality in the microbial fat/oil production, virtually no publications can be found currently which relate to such process development.

Drying processes can be generally classified into three steps or periods ("Shokuhin Kogaku Kiso Koza (6) Concentration and drying", R. Matsuno et al., Korin Press (1988), Chap. 5). First, if the material has an adequate moisture content, evaporation of water from the material is considered to be equivalent to evaporation of water from the water droplet surfaces, and the material temperature will shift toward the wet-bulb temperature during a period known as the pre-heating period. After the material has reached the wet-bulb temperature, the influx heat quantity from the air is completely consumed by moisture evaporation, and therefore the moisture content of the material decreases in direct proportion to time. The period of constant drying rate is referred to as the constant drying rate period. With further drying, migration of water inside the material becomes the rate-limiting factor, such that the moisture evaporation rate decreases and the moisture content reaches equilibrium with the dry air, eventually causing the drying to cease. This period is known as the falling drying rate period.

Practical drying methods may be largely divided into convection heating methods, conduction heating methods and radiation heating methods. The known radiation heating methods include infrared radiation methods, but such methods are not commonly employed for food processing involving large-scale bulk treatment, and instead convection and conduction heat methods are more widely used.

A convection heating type drier supplies hot air to rapidly remove evaporated moisture from the raw material vicinity, and thus powerfully promotes moisture evaporation; it is therefore an effective means for achieving massive moisture content reduction. On the other hand, however, the large hot air supply causes scattering of the dried material powder and raises the energy costs for the fans, while raw materials with high moisture contents lead to problems such as clumping due to adhesion among the materials, and reduced hot air contact area.

A conduction heating type drier can achieve high heat efficiency with virtually no air flow, and therefore blowing energy costs and scattering of raw material dust can be vastly reduced. On the other hand, however, heating occurs by heat conduction alone and thus it has been difficult to accomplish drying to a low moisture content.

Japanese Unexamined Patent Publication SHO No. 63-44891

Japanese Unexamined Patent Publication SHO No. 63-12290

Japanese Unexamined Patent Publication No. 2003-48831

Japanese Unexamined Patent Publication HEI No. 06-153970

Japanese Domestic Re-publication No. 98/029558

WO97/36996

CN1323904A

Industrial applications of single cell oils, edited by D. J. Kyle and C. Ratledge, AOCS press (1992) p. 118-138

Shokuhin Kogaku Kiso Koza (6) Concentration and drying", R. Matsuno et al., Korin Press (1988), Chap. 5

DISCLOSURE OF THE INVENTION

Thus, in consideration of moisture behavior during the three periods of the drying process, the pre-heating period, constant drying rate period and falling drying rate period, it is highly desirable to develop a novel process suitable for drying of microbial biomasses, which is based on comprehensive examination of the advantages and disadvantages of driers largely classified as convection heating systems and/or conduction heating systems.

The present inventors conducted diligent research on procedures for recovering microbial biomasses during production of PUFA-containing fat and/or oil production by microbial fermentation, and discovered that by employing several means based on different principles, and particularly a combination of a conduction heating system and convection heating system, for the drying step, the advantages of each of the heating systems can be utilized to overcome the drawbacks and significantly improve economy of the drying step. It was further discovered that by cooling the dried mycelia during the period after drying and before filling and packaging, it is possible to obtain a PUFA-containing crude oil of desirable quality.

According to the invention, therefore, there are provided a novel drying method incorporating a plurality of methods, as well as a method for production and a method for storage of PUFA-containing fats and/or oils (triglycerides) and/or PUFA-containing phospholipids and PUFA-containing mycelia characterized by filling and packaging dried mycelia after cooling them.

Specifically, the present invention provides a method for isolating one compound or more than one compounds from a microbial biomass which contains microorganisms that have produced the compound or compounds, the method comprising the following steps:

(a) preparing or obtaining wet cells having an average moisture content of between 30% and 80%;

(b) subjecting the wet cells to primary drying to obtain primary dried cells having an average moisture content of between 5% and 50%;

(c) subjecting the primary dried cells obtained in (b) to secondary drying to obtain secondary dried cells having an average moisture content of no greater than 10%; and (d) extracting or isolating, purifying and/or refining the compound or each of the compounds from the secondary dried cells obtained in (c).

In the method described above, the primary drying in (b) is accomplished with a conduction heating system, which is preferably a conical ribbon mixing drier, a conduction heat transfer drier, a drum drier or a cyclone drier. The secondary drying in (c) is accomplished with a convection heating system, for example, such as a vibrating fluidized bed drier, a horizontal continuous fluidized bed drier, a rotary drier, a box-type parallel flow drier, a box-type air flow drier, a vibrating drier/cooler, a fluidized bed drier, a band-type air flow drier or a band drier. Preferably, the wet cells in (a) are obtained by solid/liquid separation of a culturing solution, and the solid/liquid separation is preferably carried out simultaneously with mechanical dehydration.

The biomass, for example, contains a fungus or is derived from a fungus. The fungus may be one, for example, belonging to the order Mucorales and the genus *Mortierella*, such as *Mortierella alpina*.

The biomass may contain an alga or be derived from an alga. The alga may belong, for example, to the genus *Crypthecodinium, Thrautochytrium, Schizochytrium, Ulkenia, Japonochytrium* or *Haliphthoros*.

For example, the alga may be *Crypthecodinium cohnii*.

The compound is preferably a fat or oil comprising a polyunsaturated fatty acid as a constituent fatty acid, where the polyunsaturated fatty acid is a C18 or greater ω3, ω6 and/or ω9 fatty acid having two or more double bonds, and for example, α-linolenic acid (9,12,15-octadecatrienoic acid), 6,9,12,15-octadecatetraenoic acid (18:4ω3), 8,11,14,17-eicosatetraenoic acid (20:40ω3), EPA (5,8,11,14,17-eicosapentaenoic acid), DPAω3 (7,10,13,16,19-docosapentaenoic acid), DHA (4,7,10,13,16,19-docosahexaenoic acid), γ-linolenic acid (6,9,12-octadecatrienoic acid), dihomo-γ-linolenic acid (8,11,14-eicosatrienoic acid), arachidonic acid (5,8,11,14-eicosatetraenoic acid), 7,10,13,16-docosatetraenoic acid (22:4 ω6), DPAω6 (4,7,10,13,16-docosapentaenoic acid), 6,9-octadecadienoic acid (18:2ω9), 8,11-eicosadienoic acid (20:20ω9) and/or Mead acid (5,8,11-eicosatrienoic acid).

According to a preferred mode of the method described above, the secondary dried cells obtained in step (c) are supplied to step (d) after cooling treatment by one of the following methods:

(i) cooling to at least 60° C. by supplying air having a composition with an oxygen concentration of no greater than 21%; or (ii) cooling to at least 60° C. by static cooling in an atmosphere of air having a composition with an oxygen concentration of no greater than 21%.

The invention further provides a method for obtaining one compound or more than one compounds from dried cells containing a microbial biomass that have produced the compound or compounds, the method comprising the following steps:

(a) preparing or obtaining wet cells having an average moisture content of between 30% and 80%;

(b) subjecting the wet cells to primary drying to obtain primary dried cells having an average moisture content of between 5% and 50%;

(c) subjecting the primary dried cells obtained in (b) to secondary drying to obtain secondary dried cells having an average moisture content of no greater than 10%.

According to the method described above, for example, the primary drying in (b) is accomplished with a conduction heating system and the secondary drying in (c) is accomplished with, for example, a convection heating system.

The invention still further provides a method for storing dried mycelia comprising a microbial biomass containing a microorganism which has produced one compound or more than one compounds, wherein (1) dried mycelia are obtained by the following steps:
(a) preparing or obtaining wet cells having an average moisture content of between 30% and 80%;
(b) subjecting the wet cells to primary drying to obtain primary dried cells having an average moisture content of between 5% and 50%;
(c) subjecting the primary dried cells obtained in (b) to secondary drying to obtain secondary dried cells having an average moisture content of no greater than 10%; and then (2) the obtained secondary dried cells are subjected to cooling treatment by one of the following methods:
(i) cooling to at least 60° C. by supplying air having a composition with an oxygen concentration of no greater than 21%; or
(ii) cooling to at least 60° C. by static cooling in an atmosphere of air having a composition with an oxygen concentration of no greater than 21%; and (3) the cooled secondary dried cells are stored by one of the following methods:
(I) filling the cells into a sealable container together with nitrogen gas and storing them at 15° C. or below; or
(II) filling the cells into a sealable container together with air having an oxygen concentration of no greater than 20%, and storing them at 15° C. or below.

In the method described above, for example, the primary drying in (b) is accomplished with a conduction heating system and the secondary drying in (c) is accomplished with, for example, a convection heating system.

The invention still further provides the use of a compound which has been isolated, extracted, purified or refined by the method described above, for production of a food composition, functional food, nutritional supplement, preterm infant formula, term infant formula, nursing infant formula, nursing infant food, maternal food, geriatric food, cosmetic and/or pharmaceutical composition. The invention also provides the use of a compound which has been isolated, extracted, purified and/or refined by the method described above for production of an animal feed, fish feed and/or plant fertilizer.

EMBODIMENTS FOR CARRYING OUT THE INVENTION

The present invention relates to a method for production of dried mycelia containing PUFA-containing fats and/or oils and/or PUFA-containing phospholipids, and/or PUFA-containing fats and/or oils and/or PUFA-containing phospholipids, by culturing of a microorganism capable of producing compounds comprising polyunsaturated fatty acids as constituent fatty acids (PUFA-containing fats and/or oils and/or PUFA-containing phospholipids).

Thus, culturing of a microorganism capable of producing compounds comprising polyunsaturated fatty acids as constituent fatty acids (fats/oils (triglycerides) and/or phospholipids) is essential. The microorganism referred to here is preferably a microorganism which produces at least one type of polyunsaturated fatty acid from among C18 or greater ω6 polyunsaturated fatty acids having three or more double bonds, C18 or greater ω9 polyunsaturated fatty acids having two or more double bonds and C18 or greater ω3 polyunsaturated fatty acids having three or more double bonds, as the major constituent fatty acid of the triglycerides and/or phospholipids.

As C18 or greater ω6 polyunsaturated fatty acids having three or more double bonds there may be mentioned γ-linolenic acid (6,9,12-octadecatrienoic acid), dihomo-γ-linolenic acid (8,11,14-eicosatrienoic acid), arachidonic acid (5,8,11, 14-eicosatetraenoic acid), 7,10,13,16-docosatetraenoic acid (22:4 ω6) and DPAω6 (4,7,10,13,16-docosapentaenoic acid), as C18 or greater ω9 polyunsaturated fatty acids having two or more double bonds there may be mentioned 6,9-octadecadienoic acid, 8,11-eicosadienoic acid and Mead acid (5,8,11-eicosatrienoic acid), and as C18 or greater ω3 polyunsaturated fatty acids having three or more double bonds there may be mentioned α-linolenic acid (9,12,15-octadecatrienoic acid), 6,9,12,15-octadecatetraenoic acid (18:4ω3), 8,11,14, 17-eicosatetraenoic acid (20:40ω3), EPA (5,8,11,14,17-eicosapentaenoic acid), DPAω3 (7,10,13,16,19-docosapentaenoic acid) and DHA (4,7,10,13,16,19-docosahexaenoic acid).

According to the invention, therefore, any microorganism may be used which can produce a compound comprising a polyunsaturated fatty acid as a constituent fatty acid (fat/oil (triglyceride) and/or phospholipid). As examples of microorganisms capable of producing oils and/or fats (triglycerides) containing arachidonic acid as a constituent fatty acid there may be mentioned microorganisms belonging to the genera *Mortierella, Conidiobolus, Pythium, Phytophthora, Penicillium, Cladosporium, Mucor, Fusarium, Aspergillus, Rhodotorula, Entomophthora, Echinosporangium* and *Saprolegnia*.

As examples of microorganisms belonging to the genus *Mortierella*, subgenus *Mortierella*, there may be mentioned *Mortierella elongata, Mortierella exigua, Mortierella hygrophila* and *Mortierella alpina*. More specifically, there may be mentioned the strains *Mortierella elongata* IFO8570, *Mortierella exigua* IFO8571, *Mortierella hygrophila* IFO5941, and *Mortierella alpina* IFO8568, ATCC16266, ATCC32221, ATCC42430, CBS219.35, CBS224.37, CBS250.53, CBS343.66, CBS527.72, CBS529.72, CBS608.70, CBS754.68, etc.

As examples of microorganisms capable of producing DHA there may be mentioned microorganisms belonging to the genera *Crypthecodinium, Thrautochytrium, Schizochytrium, Ulkenia, Japonochytrium* and *Haliphthoros*.

All of these strains may be acquired without any special restrictions from the Institute for Fermentation, Osaka (IFO), American Type Culture Collection (ATCC) or Centralbureau voor Schimmelcultures (CBS). There may also be used the strains *Mortierella alpina* 1S-4 and *Mortierella elongata* SAM0219 (FERM BP-1239) (internationally deposited under the provisions of the Budapest Treaty on Mar. 19, 1986, with the International Patent Microorganism Depository of National Institute of Advanced Industrial Science and Technology, of Chuo 6, 1-1, Higashi 1-chome, Tsukuba city, Ibaraki pref., Japan) (FERM P-8703 deposited in Japan on Mar. 19, 1986, was transferred to international deposition), isolated from soil by the research group for the present invention.

For culturing of a strain to be used for the invention, vegetative cells, spores and/or hyphae of the strain, a seed culture solution obtained by pre-culturing the strain, or vegetative cells, spores and/or hyphae collected from seed culturing, may be seeded in a liquid medium or solid medium for culturing. The carbon source used may be a common one such as glucose, fructose, xylose, saccharose, maltose, soluble starch, molasses, glycerol, mannitol or saccharified starch, although there is no limitation to these.

As nitrogen sources there may be used natural nitrogen sources such as peptone, yeast extract, malt extract, meat extract, casamino acid, corn steep liquor, soybean protein, defatted soybean and cotton seed meal, as well as organic nitrogen sources including urea or inorganic nitrogen sources such as sodium nitrate, ammonium nitrate and ammonium sulfate, among which there may be specifically mentioned nitrogen sources obtained from soybean, and particularly soybean, defatted soybean, soybean flakes, edible soybean protein, okara, soy milk, soy flour and the like. Especially preferred for use is heat denatured defatted soybean, and more preferably one or more different types of defatted soybean heat treated at about 70-90° C. and depleted of the ethanol-soluble components, optionally in combination with any of the nitrogen sources mentioned above.

If necessary, trace nutrients including phosphate ion, potassium ion, sodium ion, magnesium ion or calcium ion, metal ions such as iron, copper, zinc, manganese, nickel or cobalt, or vitamins may also be added. Such medium components are not particularly restricted so long as they are in concentrations which do no interfere with growth of the microorganism. For practical applications, the carbon source may be added at a total concentration of 0.1-40 wt % and preferably 1-25 wt % and the nitrogen source at a total concentration of 2-15 wt % and preferably 2-10 wt %, and especially an initial carbon source addition of 1-5 wt % and an initial nitrogen source addition of 3-8 wt %, with further feeding of the carbon and nitrogen sources (more preferably the carbon source alone) during culturing.

The yield of the PUFA-containing fat or oil can be increased by using an unsaturated fatty acid precursor, for example, a hydrocarbon such as hexadecane or octadecane; a fatty acid such as oleic acid or linoleic acid or a salt thereof, a fatty acid ester such as an ethyl ester, glycerin fatty acid ester or sorbitan fatty acid ester, or a fat or oil such as olive oil, soybean oil, rapeseed oil, cottonseed oil or coconut oil, either alone or in combinations. Addition of the substrate may be at 0.001-10% and preferably 0.05-10% with respect to the medium. Such substrates may also be used as the sole carbon source for culturing.

The culturing temperature for the microorganism which produces the PUFA-containing fat or oil will differ depending on the microorganism used, and may be 5-40° C. and preferably 20-30° C., or cells grown by culturing at 20-30° C. may be subsequently cultured at 5-20° C. to produce PUFA-containing fats and oils. Such temperature control can also increase the proportion of PUFAs of the constituent fatty acids in the PUFA-containing fats and/or oils. Seed culturing may be carried out by jar fermentor culturing, shake culturing, stationary liquid culturing or solid culturing, and jar fermentor culturing is carried out for the main culturing. The medium pH at the start of the main culturing (upon transfer of the seed culture) is adjusted to 5-7, and preferably 5.5-6.5. The culturing period for each stage of seed culturing will normally be 1-10 days, preferably 1-5 days and more preferably 1-3 days. The culturing period for the main culturing will normally be 2-30 days, preferably 5-20 days and more preferably 5-15 days.

Microorganisms belonging to the genus *Mortierella* subgenus *Mortierella* are known to produce compounds comprising arachidonic acid as the main constituent fatty acid (fats and/or oils (arachidonic acid-containing triglycerides) and/or arachidonic acid-containing phospholipids), but through mutagenesis of the aforementioned strain, the present inventors have succeeded in obtaining a microorganism capable of producing fats and oils comprising dihomo-γ-linolenic acid as the main constituent fatty acid (Japanese Unexamined Patent Publication HEI No. 5-91887), and microorganisms capable of producing fats and oils comprising ω9 polyunsaturated fatty acids as the main constituent fatty acids (Japanese Unexamined Patent Publication HEI No. 5-91888, Japanese Unexamined Patent Publication HEI No. 10-57085, Japanese Unexamined Patent Publication HEI No. 5-91886).

In addition, we have obtained microorganisms having resistance to high-concentration carbon sources (WO98/39468), which microorganisms belong to the genus *Mortierella* subgenus *Mortierella* and can produce PUFA-containing cells and/or PUFA-containing fats and oils by the production method of the invention. However, the present invention is not limited to microorganisms belonging to the genus *Mortierella* subgenus *Mortierella*, and the production method of the invention may be applied to microorganisms capable of producing compounds comprising polyunsaturated fatty acids as constituent fatty acids (fats and/or oils (triglycerides) and/or phospholipids), to obtain dried cells having the PUFA-containing fats and/or oils and/or PUFA-containing phospholipids in the cells, and to obtain those fats and oils (crude oils and/or refined fats and/or oils) and/or phospholipids (crude phospholipids and/or refined phospholipids).

The method for obtaining the crude oil and/or crude phospholipid from microorganisms having the fat or oil accumulated in the mycelia may involve treating the fully cultured solution directly or after sterilization, concentration and acidification, and then recovering the cultured cells by ordinary solid/liquid separation means such as natural precipitation, centrifugal separation and/or filtration. The solid/liquid separation can be aided by addition of an aggregating agent or filtering aid. Examples of aggregating agents include aluminum chloride, calcium chloride, algin and chitosan. Diatomaceous earth may be mentioned as a filtering aid.

The recovered cultured mycelia are then dried. Drying can prevent putrefaction, oxidative degradation and hydrolysis during storage of the mycelia. It can also increase the efficiency of crude oil extraction from the mycelia.

The drying method is characterized by comprising a combination of primary drying by a conduction heating system and secondary drying with a convection heating system.

There are no particular restrictions on the drying with a conduction heating system, so long as the drier employs conduction heating as the main heat source, but a thermal adhesion conveyor type is preferred, and a drum drier is more preferred. The heating temperature on the conduction surface is 100-200° C., preferably 105-170° C. and more preferably 120-150° C. for heating to dryness. When a double drum drier is used for the primary drying, the primary dried cells have a dried sheet-like cell surface layer resulting from the conduction heating, and scraping can produce a flaky form of non-controlled shape. More specifically, the flakes have a thickness of 0.05-4 mm and preferably 0.1-1 mm, with lengths and widths (the lengths of the sides of circumscribed quadrilaterals) of 1-100 mm, preferably 1-40 mm and more preferably 2-20 mm. The primary dried cells having the dried cell surface layer can be efficiently supplied for the subsequent secondary drying with a convection heating system.

The microbial biomass (having a dried cell surface layer) obtained from the primary drying with a conduction heating system is supplied for drying with a convection heating system. The drying with the convection heating system is not particularly restricted so long as the drier employs convection heating as the main heat source, but it is preferred to use a material transport type, a material agitating type or hot air transport type, and more preferably an aerobic band material transport type or a fluidized bed or vibrating fluidized bed material agitating type. The hot air temperature on the convection surface is 40-200° C., preferably 60-170° C. and more preferably 80-150° C. as the supplied hot air temperature for drying.

Since a convection heating type drier rapidly removes evaporated moisture from the vicinity of the raw material by supply of hot air, it is considered to be an effective means when a large reduction in moisture content is desired. On the other hand, however, the large hot air supply causes scattering of the dried material powder and raises the energy costs for the blowing fans, while raw materials with high moisture contents lead to problems such as clumping due to adhesion among the materials, and reduced hot air contact area.

A conduction heating type drier can achieve high heat efficiency with virtually no air flow, and therefore blowing energy costs and flying of raw material dust can be vastly reduced. On the other hand, however, since heating occurs by heat conduction alone it has been difficult to accomplish drying to a low moisture content. Therefore, a system which utilizes the advantages of both types was newly contrived, whereby drying is carried out by a conduction heating system from the pre-heating period to the constant drying rate period during which time the moisture content of the material is higher, and drying is carried out by a convection heating system from the constant drying rate period to the falling drying rate period, during which time the moisture content is lower.

For example, a double drum drier method, one type of conduction heating system, allows the moisture content to be drastically reduced in the primary drying, while drying of the cell surface layer prevents clumping due to adhesion among the materials, and reduced hot air contact area, during the secondary drying. Furthermore, since it is possible to minimize the hot air volume and/or hot air treatment time in the drying step with the convection heating system, compared to the conventional methods which do not employ primary drying, a reduction in scattering off and fuel expenses may be expected, and therefore this method is superior to the conventional methods.

The machines used for the cell drying are not particularly restricted so long as they are conduction and convection heating systems, but the following may be mentioned as specific examples. Still, the present invention is not limited to these specific machines, and any other apparatuses which work on the same drying principles may be used without any special restrictions.

As conduction heating type machines there may be mentioned the following:
  Conical ribbon mixing drier, Ookawara Mfg. Co., Ltd.
  Conduction heat transfer drier, Ookawara Mfg. Co., Ltd.
  Drum drier, Yamamoto Giken Koki Co., Ltd.
  Cyclone drier, Okadara Co., Ltd.

As convection heating type machines there may be mentioned the following:
  Vibrating fluidized bed drier, Dalton Co., Ltd.
  Horizontal continuous fluidized bed drier, Dalton Co., Ltd.
  Rotary drier, Dalton Co., Ltd.
  Box-type parallel flow drier, Dalton Co., Ltd.
  Box-type air flow drier, Dalton Co., Ltd.
  Vibrating drier/cooler, Shinko Denki Co., Ltd.
  Fluidized bed drier, Ookawara Mfg. Co., Ltd.
  Band-type air flow drier, Ookawara Mfg. Co., Ltd.
  Band drier, Daiwa Sanko Mfg. Co., Ltd.

After the cells have been dried, the PUFA-containing crude oils and/or PUFA-containing crude phospholipids are recovered. The means for recovering the crude oil and/or crude phospholipids may be an organic solvent extraction method or a pressing method, but extraction with an organic solvent under a nitrogen stream is preferred. As organic solvents there may be used ethanol, hexane, methanol, chloroform, dichloromethane, petroleum ether, acetone and the like, or there may be employed alternating extraction with methanol and petroleum ether, or a single-layer solvent system of chloroform-methanol-water. However, the extraction method used to obtain the crude oil and/or crude phospholipid is not limited to the method described above and may instead be any method which accomplishes efficient extraction of cellular fats and oils (triglycerides) and/or phospholipids. For example, extraction with a supercritical $CO_2$ flow may be employed as an effective means.

By reduced pressure removal of the organic solvent or the supercritical flow components from the extract obtained by extraction using the organic solvent or supercritical flow, it is possible to obtain the target crude oil and/or crude phospholipids.

The dried cells containing the compounds comprising polyunsaturated fatty acids as constituent fatty acids (PUFA-containing fats and oils and/or PUFA-containing phospholipids) obtained according to the invention, or the crude oils (PUFA-containing crude oils) and/or crude phospholipids (PUFA-containing crude phospholipids), may be used directly by incorporation into animal feeds. For applications to foods, however, a common fat/oil purification process is preferably used to obtain a PUFA-containing refined fat/oil. The fat/oil purification process used may be an ordinary process such as degumming, deoxidation, deodorization, decolorizing, column treatment, molecular distillation, wintering or the like.

An unlimited number of uses exist for microbial biomasses, dried cells containing fats and oils (triglycerides) and/or phospholipids, crude oils, refined fats and oils (triglycerides), crude phospholipids and refined phospholipids: for example, they may be used as starting materials and additives for foods, beverages, cosmetics and pharmaceuticals. The purposes of use and amounts of use are also completely unrestricted.

As examples of food compositions there may be mentioned ordinary foods, as well as functional foods, nutritional supplements, preterm infant formula, term infant formula, nursing infant formula, infant foods, maternal foods or geriatric foods. As examples of fat/oil-containing foods there may be mentioned natural fat/oil-containing foods such as meat, fish and nuts, foods to which fats/oils are added during preparation, such as soups, foods employing fats/oils as heating media, such as donuts, fat and oil foods such as butter, processed foods to which fats/oils are added during processing, such as cookies, or foods which are sprayed or coated with fats/oils upon finishing, such as hard biscuits. Such compositions may also be added to agricultural foods, fermented foods, livestock feeds, marine foods and beverages which contain no fats or oils. They may also be in the form of functional foods or pharmaceuticals, and for example, in processed form such as enteral nutrients, powders, granules, lozenges, oral solutions, suspensions, emulsions, syrups and the like.

EXAMPLES

The present invention will now be explained in greater detail by the following examples, with the understanding that the invention is not limited thereto.

Example 1

Fluidized Bed Cooling of Dried Cells

A spore suspension of *Mortierella alpina* 1S-4 was transferred at 1.0 vol % to a medium containing 1.0% yeast extract and 2.0% glucose at pH 6.3, and seed culturing (first stage) was commenced under conditions with 100 rpm reciprocal shaking, 28° C. temperature for 3 days of culturing.

Next, 30 L of medium at pH 6.3 containing 1% yeast extract, 2% glucose and 0.1% soybean oil was prepared in a 50 L jar fermentor culturing tank, and then the seed culture (first stage) was transferred thereinto to commence seed culturing (second stage) under conditions with 200 rpm agitation, 28° C. temperature, 150 kPa internal tank pressure, for 2 days of culturing.

Next, 4500 L of a medium (medium A: 336 kg soybean flour, 16.8 kg $KH_2PO_4$, 2.8 kg $MgCl_2.6H_2O$, 2.8 kg $CaCl_2.2H_2O$, 5.6 kg soybean oil) was adjusted to pH 4.5 and sterilized at 121° C. for 20 minutes. As a separate medium, 1000 L of medium (medium B: 112 kg hydrous glucose) was sterilized at 140° C. for 40 seconds and added to the previous medium A to prepare medium C. After adding sterilized aqueous sodium hydroxide to medium C to adjust the pH to 6.1, a 28 L volume of the seed culture (second stage) was transferred thereinto and combined with the total 5600 L of initial culturing solution (10 kL culturing tank volume). The culturing was initiated at a temperature of 26° C., at an air flow of 49 $Nm^3$/hr and an internal pressure of 200 kPa. During the culturing, medium was fed according to the schedule shown in the table below, for a total of 306 hours of main culturing. Upon completion of the culturing, the culture solution volume was 7730 L, as a consequence of increase due to medium feeding and decrease due to evaporation.

| Main culturing time | Feeding medium |
| --- | --- |
| 19th hr | 280 kg/460 L hydrous glucose |
| 43rd hr | 280 kg/450 L hydrous glucose |
| 67th hr | 252 kg/390 L hydrous glucose |
| 91st hr | 252 kg/410 L hydrous glucose |
| 120th hr | 224 kg/370 L hydrous glucose |
| 140th hr | 168 kg/280 L hydrous glucose |
| 163rd hr | 168 kg/270 L hydrous glucose |

After completion of the culturing and sterilization at 120° C. for 20 minutes, the wet cells were recovered using a continuous dehydrator and disrupted, and then drying was carried out by hot air drying (hot air temperature: 120° C.) with a vibrating fluidized bed drier to a moisture content of 1 wt %. The dried cells were cooled to 40° C. by supplying room temperature air in the fluidized bed, and then an air conveyor was used to convey the dry cells to the filling zone. The obtained dry cells were filled together with nitrogen gas into an aluminum pouch container bag having a volume of about 1 $m^3$, and the bag opening was heat sealed prior to storage in a refrigerator at below 10° C.

The dry cells in the container bag were subjected to hexane extraction, and then the hexane solution was filtered to remove the solid portion and heated under reduced pressure to remove the hexane, in order to obtain a crude oil comprising arachidonic acid as a constituent fatty acid.

Example 2

Static Cooling of Dry Cells

After culturing and sterilization by the same method as in Example 1, cell recovery and drying were carried out also in the same manner as Example 1. The dry cells were transferred to a flat vat and evenly spread to a layer thickness of no greater than 1 cm, for static cooling at room temperature. Upon cooling to 50° C., they were filled together with nitrogen gas into an aluminum pouch container bag having a volume of about 200 L, and the bag opening was heat sealed prior to storage in a refrigerator at below 10° C.

Comparative Example 1

Filling of Dry Cells without Cooling

After culturing and sterilization by the same method as in Example 1, cell recovery and drying were carried out also in the same manner as Example 1. The dry cells were filled together with nitrogen gas into an aluminum pouch container bag having a volume of about 200 L, and the bag opening was heat sealed prior to storage in a refrigerator at below 10° C.

Example 3

Analysis of Dry Cells

The filled container bags prepared in Example 1, Example 2 and Comparative Example 1 were opened one week after filling, and the outer appearance of the dry cells was confirmed. The crude oil was then subjected to extraction by a Soxhlet extraction method using n-hexane as the solvent, to determine the oil content. The peroxide value (POV) of the crude oil extracted by the method of Example 1 was also analyzed.

It was thereby confirmed that when filling was carried out without cooling as in Comparative Example 1, the cells and oil portions underwent drastic reduction in quality.

TABLE 1

|  | Cells of Example 1 | Cells of Example 2 | Cells of Comparative Example 1 |
| --- | --- | --- | --- |
| Cell outer appearance | Same as time of filling (brown pulverized state) | Same as time of filling (brown pulverized state) | Different from time of filling (dark brown masses) |
| Oil content (wt %) | 55% | 53% | 20% |
| Crude oil outer appearance | yellow | yellow | brown |
| Crude oil POV (meq/kg) | 0.7 meq/kg | 1.0 meq/kg | 200 meq/kg |

Example 4

Comparison Between Prior Art Method of Supplying Granulated Microbial Biomass for Drying, and Present Invention Method of Drying Microbial Biomass by Conduction Heating System and Convection Heating System After culturing the arachidonic acid-producing strain *Mortierella alpina* 1S-4 in the same manner as Example 1, it was supplied to a continuous dehydrator (SEKISUI CS-1 by Yanagawa Engineering) for filtering, to obtain a wet cell mass. The moisture content of the wet cells was measured by the drying loss method (105° C. temperature), which indicated a moisture content of 52%. The wet cell mass was then dried under the following conditions (Experiments 4-1 to 4-2): Experiment 4-1 employed granulation molding at room temperature, and therefore no change in moisture content was seen before and after molding. In Experiment 4-2, primary drying was accomplished with a double drum drier.

Next, the granulated cells and primary dried cells were supplied to a fluidized bed drier for drying to a moisture content of approximately 2%. The dried cells were cooled by the method of Example 2, and then the fat/oil portion was extracted and the outer appearance and peroxide value were determined. Both had satisfactory outer appearances and POV values of 10 meq/kg or lower, thus indicating that crude starting oils had been obtained which were satisfactory for production of refined fats/oils. The drying time and drying yield were superior in Experiment 4-2 in which drying was carried out in two stages, compared to Experiment 4-1 in which drying was in a single stage.

TABLE 2

|  | Experiment 4-1 | Experiment 4-2 |
| --- | --- | --- |
| Primary processing machine | Extraction granulator | Double drum drier |
| Primary processing temperature | Room temperature (no primary drying) | Primary drying at drum surface temperature of 140° C. |
| Form of primary processed product | Granular Granule size: ~2-3 mm | Non-controlled form (flakes) |
| Molded product moisture content | 52% | 21% |
| ↓Secondary drying with fluidized bed drier (dry hot air temperature: 120° C.) | | |
| Time required for drying | 20 min | 11 min |
| Dry product moisture content | 2.0% | 1.9% |
| Dry yield* | 92% | 94% |

*Dry yield (%) = dried volume (as dry matter)/starting material loading volume (as dry matter) × 100

The invention claimed is:

1. A method for isolating one compound or more than one compound from a microbial biomass which contains microorganisms that have produced the compound or compounds, the method comprising the following steps:
    (a) preparing or obtaining wet cells having an average moisture content of between 30% and 80%;
    (b) subjecting the wet cells to primary drying to obtain primary dried cells having an average moisture content of between 5% and 50%, wherein the primary drying is accomplished with a conduction heating system of a thermal adhesion conveyor drier;
    (c) subjecting the primary dried cells obtained in (b) to secondary drying to obtain secondary dried cells having an average moisture content of no greater than 10%, wherein the secondary drying is accomplished with a convection heating system; and
    (d) extracting, isolating, purifying and/or refining the compound or each of the compounds from the secondary dried cells obtained in (c),
    wherein said compound or each of the compounds is a triglyceride and/or phospholipid comprising a polyunsaturated fatty acid as a constituent fatty acid.

2. The method according to claim 1, wherein said thermal adhesion conveyor drier is a double drum drier.

3. The method according to claim 1, wherein said convection heating system is a vibrating fluidized bed drier, a horizontal continuous fluidized bed drier, a rotary drier, a box-type parallel flow drier, a box-type air flow drier, a vibrating drier/cooler, a fluidized bed drier, a band-type air flow drier, or a band drier.

4. The method according to claim 1, wherein the wet cells in (a) are obtained by solid/liquid separation of a culturing solution.

5. The method according to claim 4, wherein said solid/liquid separation is carried out simultaneously with mechanical dehydration.

6. The method according to claim 1, wherein said biomass contains a fungus or is derived from a fungus.

7. The method according to claim 6, wherein said fungus belongs to the order *Mucorales*.

8. The method according to claim 6, wherein said fungus belongs to the genus *Mortierella*.

9. The method according to claim 6, wherein said fungus is *Mortierella alpina*.

10. The method according to claim 1, wherein said biomass contains an alga or is derived from an alga.

11. The method according to claim 10, wherein said alga belongs to the genus *Crypthecodinium, Thraustochytrium, Schizochytrium, Ulkenia, Japonochytrium* or *Haliphthoros*.

12. The method according to claim 10, wherein said alga is *Crypthecodinium cohnii*.

13. The method according to claim 1, wherein said polyunsaturated fatty acid is a C18 or greater $\omega 3$, 107 6 and/or $\omega 9$ fatty acid having two or more double bonds.

14. The method according to claim 1, wherein said polyunsaturated fatty acid is α-linolenic acid (9,12,15-octadecatrienoic acid), 6,9,12,15-octadecatetraenoic acid (18:4ω3), 8,11,14,17-eicosatetraenoic acid (20:4ω3), EPA (5,8,11,14,17-eicosapentaenoic acid), DPAω3 (7,10,13,16,19-docosapentaenoic acid), DHA (4,7,10,13,16,19-docosahexaenoic acid), γ-linolenic acid (6,9,12-octadecatrienoic acid), dihomo-γ-linolenic acid (8,11,14-eicosatrienoic acid), arachidonic acid (5,8,11,14-eicosatetraenoic acid), 7,10,13,16-docosatetraenoic acid (22:4 ω6), DPAω6 (4,7,10,13,16-docosapentaenoic acid), 6,9-octadecadienoic acid (18:2ω9), 8,11-eicosadienoic acid (20:2ω9) and/or Mead acid (5,8,11-eicosatrienoic acid).

15. The method according to claim 1, characterized in that the secondary dried cells obtained in step (c) are supplied to step (d) after cooling treatment by one of the following methods:
  (i) cooling to at least 60° C. by supplying air having a composition with an oxygen concentration of no greater than 21%; or
  (ii) cooling to at least 60° C. by static cooling in an atmosphere of air having a composition with an oxygen concentration of no greater than 21%.

16. A method for obtaining one compound or more than one compound from dried cells containing a biomass of microorganisms that have produced the compound or compounds, the method comprising the following steps:
  (a) preparing or obtaining wet cells having an average moisture content of between 30% and 80%;
  (b) subjecting the wet cells to primary drying to obtain primary dried cells having an average dried moisture content of between 5% and 50%, wherein the primary drying is accomplished with a conduction heating system of a thermal adhesion conveyor drier; and
  (c) subjecting the primary dried cells obtained in (b) to secondary drying to obtain secondary dried cells having an average moisture content of no greater than 10%, wherein the secondary drying is accomplished with a convection heating system,
  wherein the compound or each of the compounds is a triglyceride and/or phospholipid comprising a polyunsaturated fatty acid as a constituent fatty acid.

17. A method for storing dried cells comprising a microbial biomass containing a microorganism which has produced one compound or more than one compound, wherein
  (1) dried cells are obtained by the following steps:
    (a) preparing or obtaining wet cells having an average moisture content of between 30% and 80%;
    (b) subjecting the wet cells to primary drying to obtain primary dried cells having an average moisture content of between 5% and 50%, wherein the primary drying is accomplished with a conduction heating system of a thermal adhesion conveyor drier;
    (c) subjecting the primary dried cells obtained in (b) to secondary drying to obtain secondary dried cells having an average moisture content of no greater than 10%, wherein the secondary drying is accomplished with a convection heating system; and then
  (2) the obtained secondary dried cells are subjected to cooling treatment by one of the following methods:
    (i) cooling to at least 60° C. by supplying air having a composition with an oxygen concentration of no greater than 21%; or
    (ii) cooling to at least 60° C. by static cooling in an atmosphere of air having a composition with an oxygen concentration of no greater than 21%; and
  (3) the cooled secondary dried cells are stored by one of the following methods:
    (I) filling said cells into a sealable container together with nitrogen gas and storing them at 15° C. or below; or
    (II) filling said cells into a sealable container together with air having an oxygen concentration of no greater than 20%, and storing them at 15° C. or below,
  wherein said compound or each of the compounds is a triglyceride and/or phospholipid comprising a polyunsaturated fatty acid as a constituent fatty acid.

* * * * *